US00PP33902P2

(12) United States Plant Patent
Grazzini

(10) Patent No.: US PP33,902 P2
(45) Date of Patent: Jan. 25, 2022

(54) ***DIANTHUS* PLANT NAMED 'G18146'**

(50) Latin Name: *Dianthus hybrida*
Varietal Denomination: G18146

(71) Applicant: Garden Genetics, Bellefonte, PA (US)

(72) Inventor: Richard A. Grazzini, Bellefonte, PA (US)

(73) Assignee: Garden Genetics llc, Bellefonte, PA (US)

( * ) Notice: Subject to any disclaimer, the term of this patent is extended or adjusted under 35 U.S.C. 154(b) by 0 days.

(21) Appl. No.: 17/354,205

(22) Filed: Jun. 22, 2021

(51) Int. Cl.
*A01H 5/02* (2018.01)
*A01H 6/30* (2018.01)

(52) U.S. Cl.
USPC ..... Plt./277
CPC ..... *A01H 6/305* (2018.05)

(58) Field of Classification Search
USPC ..... Plt./277
CPC ..... A01H 6/305; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Dianthus* plant named 'G18146' is disclosed, characterized by dark rose-violet flowers with a dark red-violet eye. Plants are Winter hardy in Zone 5 and flower continuously from May through early November at 41N latitude. Healthy plants and leaves with constant growth from center. The new variety is a *Dianthus*, normally used for outdoor ornamental purposes.

2 Drawing Sheets

Figure 1:
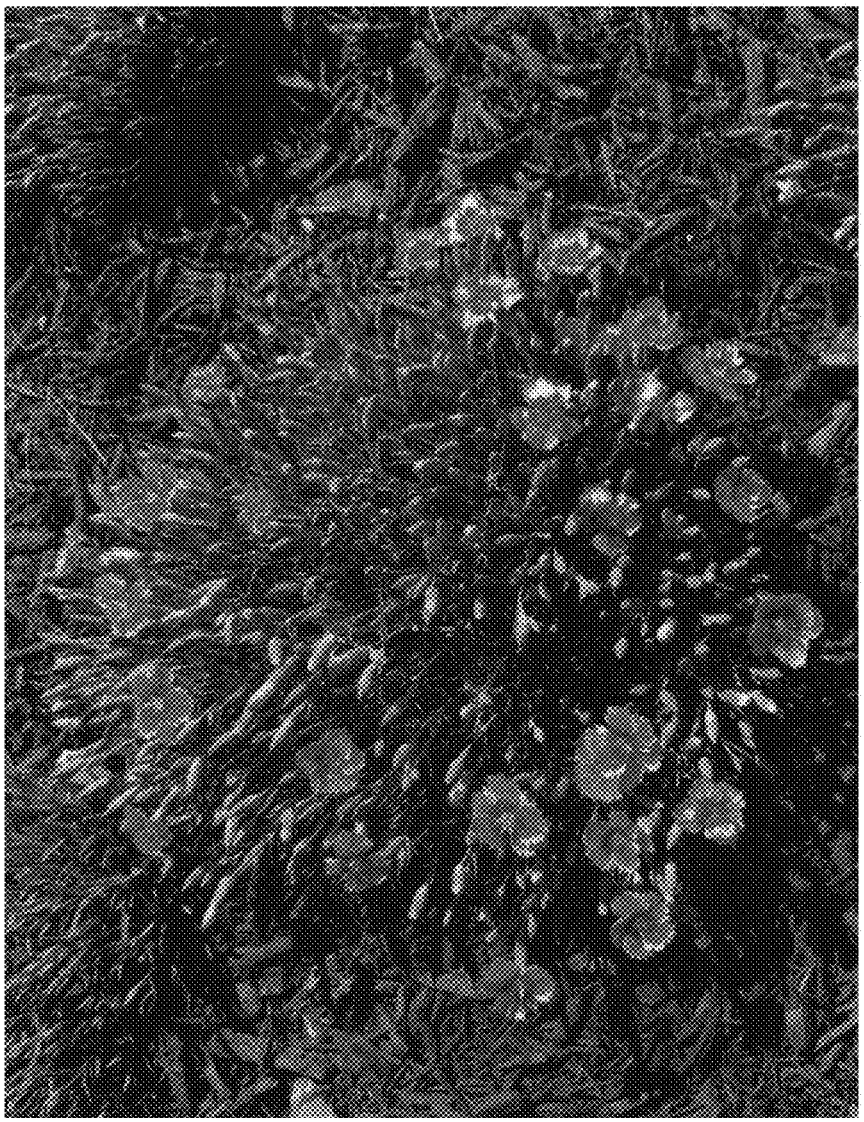

Latin name of the genus and species: *Dianthus hybrida.* Variety denomination: 'G18146'.

BACKGROUND OF THE INVENTION

The new *Dianthus* cultivar is a product of a planned breeding program conducted by the inventor at a research nursery in Bellefonte, Pa. The cross resulting in this new variety was made in December 2017.

The seed parent is the unpatented proprietary variety referred to as *Dianthus* 'G17-022'. The pollen parent is the unpatented proprietary variety referred to as *Dianthus* 'G17-014'. The new variety was selected in June of 2018 by the inventor in a group of seedlings resulting from the 2017 cross-pollination, in a nursery in Bellefonte, Pa.

Asexual reproduction of the new cultivar was performed by vegetative cuttings. This was first performed at the same nursery in in Bellefonte, Pa. during July of 2018, and has shown that the unique features of this cultivar are stable and reproduced true to type in multiple successive generations.

SUMMARY OF THE INVENTION

The cultivar 'G18146' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G18146'. These characteristics in combination distinguish 'G18146' as a new and distinct *Dianthus* cultivar:

1. Flower petals are a dark rose-violet, with a circular dark red-violet eye, and a distinct white picotee edge.
2. Flowers continuously in a greenhouse under ambient (natural) lighting.

3. Flowers constantly outdoors (in-ground) from late May thru early November at 41N latitude.
4. Large flowers on short peduncles, forming a dense floral canopy just above the foliage.
5. Good winter-hardiness (USDA z5, at least) and good winter survival.
6. Healthy plants and leaves with constant growth from center (does not form a "donut" or "birds' nest").
7. Strong field-tolerance to common *Dianthus* pathogens.

PARENT COMPARISON

Plants of the new cultivar 'G18146' are similar to plants of the seed parent in most horticultural characteristics; however, plants of the new cultivar 'G18146' differ in the following:

1. New variety 'G18146' has dark rose-violet flowers, with a circular dark red-violet "eye", and a distinct white picotee edge. Seed parent 'G17-022' has light pink flowers and a dark violet eye.
2. New variety 'G18146' has grey-green foliage. Seed parent 'G17-022' has more intense silvery-blue leaves.
3. New variety 'G18146' has short peduncles, rising between 2.0-2.5" above the foliage. Seed parent 'G17-022' has much longer peduncles, between 3.5 and 4.0" above the foliage.
4. New variety 'G18146' flowers continuously under natural light at 41N latitude. Seed parent 'G17-022' repeat-blooms, cycling in and out of flower under similar conditions.
5. New variety 'G18146' is field-tolerant of common *Dianthus* leaf and crown pathogens. Seed parent 'G17-022' is not especially tolerant, and typically dies out in the center, forming a "donut" of healthy foliage around a dead center.

Plants of the new cultivar 'G18146' are similar to plants of the pollen parent in most horticultural characteristics; however, plants of the new cultivar 'G18146' differ in the following:

1. New variety 'G18146' has dark rose-violet flowers, with a circular dark red-violet "eye", and a distinct white picotee edge. Pollen parent 'G17-014' has light pink flowers and a dark violet eye.
2. New variety 'G18146' has grey-green foliage. Pollen parent 'G17-014' has more intense silvery-blue leaves.
3. New variety 'G18146' has short peduncles, rising between 2.0-2.5" above the foliage. Pollen parent 'G17-014' has much longer peduncles, between 3.5 and 4.0" above the foliage.
4. New variety 'G18146' flowers continuously under natural light at 41N latitude. Pollen parent 'G17-014' repeat-blooms, cycling in and out of flower under similar conditions.
5. New variety 'G18146' is field-tolerant of common *Dianthus* leaf and crown pathogens. Seed parent 'G17-014' is not especially tolerant, and typically dies out in the center, forming a "donut" of healthy foliage around a dead center.

COMMERCIAL COMPARISON

Plants of the new cultivar 'G18146' are comparable to the commercial variety *Dianthus* 'WP 11 TYR04', U.S. Plant Pat. No. 25,077. The two *Dianthus* varieties are similar in most horticultural characteristics, however, the new variety 'G18146' differs in the following:

1. New variety 'G18146' has dark rose-violet flowers, with a circular dark red-violet "eye", and a distinct white picotee edge. Comparison variety 'WP 11 TYR04' has pink flower petals with a dark red eye which spreads across the petal in lines and splashes.
2. New variety 'G18146' flowers continuously under natural light at 41N latitude. Comparison variety 'WP 11 TYR04' repeat-blooms under similar conditions, but does not bloom continuously.
3. New variety 'G18146' has grey-green foliage. Comparison variety 'WP 11 TYR04' has more glaucous silver-green leaves.
4. New variety 'G18-146' has relatively short peduncles, rising 2.0-2.5" above the foliage. Comparison variety 'WP 11 TYR0O04' has slightly longer peduncles, rising about 3.0" above the leaves.

Plants of the new cultivar 'G18146' are comparable to the commercial variety *Dianthus* 'Uribest52', U.S. Plant Pat. No. 28,239. The two *Dianthus* varieties are similar in most horticultural characteristics; however, the new variety 'G18146' differs in the following:

1. New variety 'G18146' has single, light pink flowers. Comparison variety 'Uribest52' has deep red-purple flowers.
2. Flowers of variety 'G18146' have a uniformly circular medium-red eye. Comparison variety 'Uribest52' has no eye in its flowers.
3. New variety 'G18146' has large single flowers, between 1.5 and 2.0" in diameter. Comparison variety 'Uribest52' has relatively small flowers (ca. 1.0") in comparison.
4. New variety 'G18146' has longer peduncles, with flower placement between 2.0-2.5" above the leaves. Comparison variety 'Uribest52' has much shorter peduncles (1.5-2.0"), with the flowers displayed very close to the foliage canopy.

BRIEF DESCRIPTION OF THE PHOTOGRAPHS

The accompanying photograph in FIG. 1 illustrates a typical flowering plant of 'G18146' grown outdoors in Bellefonte, Pa. at approximately 4 months old in a 1-gallon pot.

Figure 2:
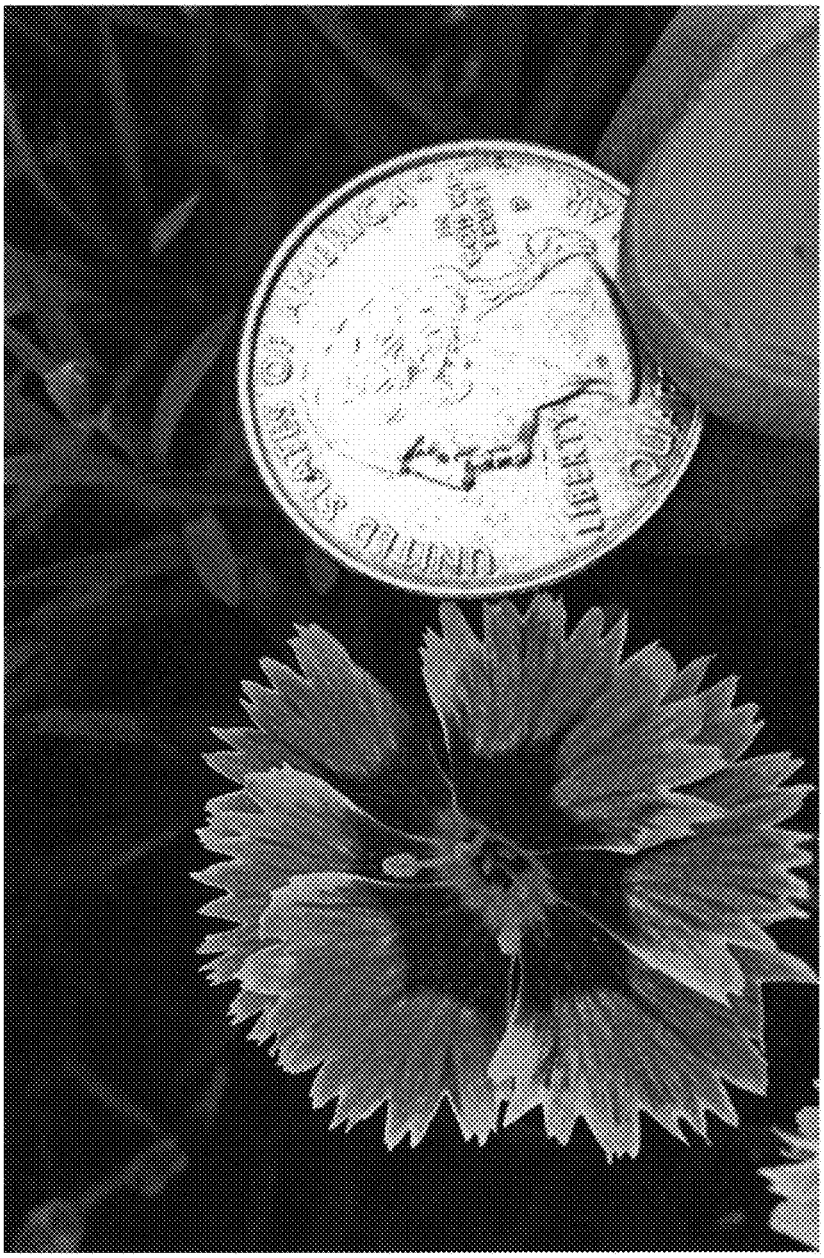

FIG. 2 illustrates a close-up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'G18146' plants grown outdoors in Camarillo, Cali. The growing temperature ranged from approximately 10° C. to 25° C. during the day and from approximately 6° C. to 12° C. during the night. General light conditions are normal sunlight and numerical values represent averages of typical plant types. Measurements were taken during June of 2021. Botanical classification: *Dianthus hybrida* 'G18146'.

PROPAGATION

Time to initiate roots: About 10 days at approximately 24° C.
Time to produce a rooted cutting: About 18 days at 24° C.
Root description: Fibrous roots, approximately 1 to 3 mm in diameter, colored near RHS Orange-White 159C.

PLANT

Age of plant described: About 10 weeks from a rooted cutting.
Growth habit: Mounded flowering perennial.
Plant spread: About 15 cm.
Plant height: About 8 cm.
Plant vigor: Strong.
Length plant stem: Average 6.5 cm.
Diameter of plant stem: Approximately 3 mm.
Quantity stems: Approximately 30 to 40.
Stem:
*Color.*—Near RHS Greyed-Green 191C.
*Texture.*—Smooth.
*Hollowness.*—Slightly hollow with age.
Internode length: 0.8 to 1.8 cm.

FOLIAGE

Leaf:
*Arrangement.*—Opposite (in pairs).
*Quantity.*—Approximately 12 to 16 fully expanded per stem.
*Average Length.*—2.5 to 4.0 cm.
*Average Width.*—3 to 4 mm.
*Shape of blade.*—Linear.
*Apex.*—Acute.
*Base.*—Clasping.
*Attachment.*—Sessile.
*Margin.*—Entire.
*Texture of top surface.*—Smooth.
*Texture of bottom surface.*—Smooth.

*Pubescence.*—None.

*Color.*—Young foliage upper side: Near RHS Greyed-Green 189B. Young foliage under side: Near RHS Greyed-Green 189B. Mature foliage upper side: Near RHS Greyed-Green 189A. Mature foliage under side: Near RHS Greyed-Green 189A.

*Venation.*—Type: Linear. Venation color upper side: Indistinguishable from foliage. Venation color under side: Indistinguishable from foliage.

FLOWER

Natural flowering season: May through early November at 41N latitude.

Inflorescence type and habit: Umbel of 2 to 3 flowers.

Flower longevity on plant: Individual flowers about 10 days.

Quantity of flowers: Approximately 20 flowers and buds on an 8-week-old plant.

Flowers persistent or self-cleaning: Persistent.

Fragrance: Faint sweet scent.

Inflorescence (Umbel) size:

*Diameter.*—Approximately 5.0 cm.

*Height.*—Approximately 5.0 cm.

Individual flower size:

*Diameter.*—Approximately 2.9 cm.

*Length.*—Approximately 2.4 cm.

Petals:

*Petal arrangement.*—Single overlapping whorl.

*Shape.*—Spatulate, elongated base.

*Base.*—Long attenuate.

*Margin.*—Serrated.

*Apex.*—Serrate.

*Length.*—Upper section, outside of tube: 1.3 cm. Elongated base, in tube, 1.6 cm.

*Width.*—Upper section, outside of tube: 1.3 cm. Elongated base, in tube, 3 mm.

*Petal quantity.*—Average range 12 to 15.

*Texture.*—Smooth all surfaces.

*Aspect.*—Nearly flat.

Color:

When opening:

*Upper surface.*—Near RHS Red-Purple N74A flushed Purple N78A, flecked Purple 75B, margins near Purple 75C. Large center eye Red-Purple 59A. Visible throat near Purple 75C.

*Lower surface.*—Near RHS Red-Purple N74B streaked Red-Purple N74C. Base near tube N74D.

Fully opened:

*Upper surface.*—Near RHS Red-Purple N74B flushed Purple N78B, flecked Purple 75B, margins near Purple 75C. Large center eye Red-Purple 59A. Visible throat near Purple 75C.

*Lower surface.*—Near RHS Red-Purple N74C streaked Purple 75C. Base near tube N74D.

Tube:

General description: Tube consists of the elongated, unfused base of the petals. Tube shape caused by a fused calyx.

*Length.*—1.5 cm.

*Width.*—5 mm.

*Texture.*—Smooth.

Color:

Fully opened:

*Inner surface.*—Near RHS Greyed-Green 189B.

*Outer surface.*—Near RHS Greyed-Green 189A.

Bud:

*Shape.*—Elongated cylinder.

*Length.*—Average 1.7 cm.

*Diameter.*—Average 0.9 cm.

*Color.*—Appearing petals colored near RHS Purple N78A.

Sepals:

*Quantity.*—5.

*Arrangement.*—Fused tube.

*Shape.*—Cylindric.

*Length.*—1.2 cm.

*Width.*—0.3 cm.

*Margin.*—Entire.

*Apex.*—Acute.

*Texture.*—Smooth upper and lower surfaces.

*Color.*—Near RHS Greyed-Green 189A.

Bracteoles:

*Shape.*—Narrow deltoid.

*Quantity per flower.*—5-7.

*Length.*—Average 5 mm.

*Width.*—Average 4 mm.

*Margin.*—Entire.

*Texture.*—Smooth.

*Color.*—Near RHS Greyed-Green 189B.

Peduncle:

*Length.*—Average 3 to 5 cm.

*Diameter.*—2.0 mm.

*Color.*—Near RHS Greyed-Green 189B.

*Orientation.*—Upright.

*Strength.*—Moderate.

*Texture.*—Smooth.

REPRODUCTIVE ORGANS

Stamens:

*Number.*—About 10.

*Filament length.*—1.3 cm.

*Filament color.*—Near RHS Purple 75C.

Anthers:

*Shape.*—Linear.

*Length.*—3 mm.

*Color.*—RHS Greyed-Purple N187D.

*Pollen.*—Not observed.

Pistil:

*Number.*—1, 2 stigmas.

*Length.*—1.7 cm.

*Style.*—Number: 2. Length: Approximately 1 cm. Color: Base near RHS Purple 76D, upper-section Purple 75C.

*Stigma.*—Shape:l Linear. Color: Near RHS Purple 75B.

*Ovary.*—Shape: Oblong. Diameter: 7 mm. Length: 7 mm. Color: Near RHS Yellow-Green 150D.

OTHER CHARACTERISTICS

Fruits and seeds: Not observed to date.

Disease/pest resistance: Shows good field-tolerance to common *Dianthus* pathogens. Specific pathogens resistance has not been determined.

Temperature range: Winter hardiness to at least USDA Zone 5.

What is claimed is:

1. A new and distinct cultivar of *Dianthus* plant named 'G18146' as herein illustrated and described.

* * * * *